US00PP30755P3

(12) United States Plant Patent
Mazzardis

(10) Patent No.: US PP30,755 P3
(45) Date of Patent: Jul. 30, 2019

(54) BLUEBERRY PLANT NAMED 'NS 14-4'

(50) Latin Name: ***Vaccinium* hybrid**
Varietal Denomination: NS 14-4

(71) Applicant: Vincent David Mazzardis, Joondalup (AU)

(72) Inventor: Vincent David Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 15/732,425

(22) Filed: Nov. 9, 2017

(65) Prior Publication Data

US 2019/0141869 P1 May 9, 2019

(51) Int. Cl.
*A01H 5/08* (2018.01)

(52) U.S. Cl.
USPC ..... Plt./157

(58) Field of Classification Search
USPC ..... Plt./157
See application file for complete search history.

*Primary Examiner* — Susan McCormick Ewoldt
(74) *Attorney, Agent, or Firm* — Randall Danskin P.S.

(57) ABSTRACT

A new and distinct variety of blueberry plant, which is denominated varietally as 'NS 14-4' is described, and which produces a fruit having a very large fruit size, high fruit firmness, medium fruit acidity, and a medium to high fruit sweetness, and displaying a small dry picking scar, and a high yield, when grown under the ecological conditions prevailing near Yanchep Springs, Yanchep, Western Australia.

3 Drawing Sheets

Latin name: '*Vaccinium*' hybrid.
Varietal denomination: 'NS 14-4'.

BACKGROUND OF THE NEW VARIETY

The present invention relates to a new, novel, and distinct variety of blueberry plant '*Vaccinium*' hybrid and which has been denominated varietally 'NS 14-4'.

ORIGIN AND ASEXUAL REPRODUCTION OF THE NEW VARIETY

The present, new variety of blueberry plant resulted from an ongoing development program of plant breeding. The purpose of this program was to improve the commercial quality of various plant varieties by creating, and releasing, promising selections of plants, including blueberries. To this end, I have made both controlled and hybrid cross-pollinations each year to produce resulting plant populations from which improved progenies are evaluated and selected.

The new blueberry plant 'NS 14-4' was derived from a controlled cross-pollination employing the blueberry plant 'SC10' (unpatented), which is the seed parent, and blueberry plant 'NS30', (unpatented), and which is the pollen parent, during the 2012 growing season. This first cross-pollination took place at my property, which is located at Yanchep Springs, Yanchep, Western Australia. The seed parent 'SC10' is characterized, at least in part, by a semi-upright growth habit, a strong vigor, an early season ripening date, and further produces large sized, firm, high sweetness, and medium acidity fruit. The pollen parent 'NS30', on the other hand, is characterized, at least in part, by a semi-upright growth habit, a medium vigor, a very early ripening date, and further produces medium sized, firm, high sweetness, and low acidity fruit. The seed derived as a result of the first cross-pollination from the seed parent, blueberry plant 'SC10', produced approximately 500 plants. These new plants were then grown at my aforementioned property, and the first fruit was evaluated during the 2014 growing season. Further, an additional assessment of these same new plants, which took place in 2014, resulted in the new variety 'NS 14-4' being selected for further asexual reproduction and evaluation. The present, new variety showed desirable traits suitable for a commercial blueberry variety. The present, new variety was asexually reproduced by vegetative cuttings at Yanchep Springs, Yanchep, Western Australia, and the plants produced from this first asexual propagation at Yanchep Springs were again evaluated during the 2014 to 2016 growing seasons. The asexually reproduced plants, which were produced from the aforementioned asexual reproduction process, were subsequently evaluated, and were found to be true to the original plant. It was my conclusion, at that time, that the variety 'NS 14-4' was a new, novel, and distinct variety of blueberry plant.

In relative comparison to two of the closest known varieties, that being the 'EB 8-1' blueberry plant (U.S. Plant Pat. No. 25,859), and 'EB 8-46' blueberry plant (U.S. Plant Pat. No. 26,173), the new variety of blueberry plant is clearly distinguishable. The present, new variety is distinguishable from the 'EB 8-1' blueberry plant (a closest known variety) in view of its bush growth habit, which expresses a semi-upright growth habit when compared to the growth habit of the 'EB 8-1' blueberry plant, which has a growth habit which is considered spreading. Further, the present, new variety is distinguishable from the 'EB 8-1' blueberry plant in view of the fruit it produces, which possesses a high fruit firmness when compared to the fruit produced by the 'EB 8-1' blueberry plant, which produces fruit having a medium fruit firmness. Still further, the present, new variety is distinguishable from the 'EB 8-1' blueberry plant (a closest known variety) in view of the fruit it produces, which possesses a very large fruit size when compared to the fruit produced by the 'EB 8-1' blueberry plant, which produces fruit having a large fruit size. Moreover, the present, new variety is distinguishable from the 'EB 8-1' blueberry plant in view of the fruit it produces, which possess a medium to high fruit sweetness when compared to the fruit produced by the 'EB 8-1' blueberry plant, which produces fruit having a medium fruit sweetness. Yet further, the present, new variety is distinguishable from the 'EB 8-1' blueberry plant (a closest known variety) in view of its bush, which does not produce flowers and fruit on the current year's shoots when compared to the bush of the 'EB 8-1' blueberry plant, which does produce flowers and fruit on the current year's shoots.

The present, new variety is distinguishable from the 'EB 8-46' blueberry plant (a closest known variety) in view of its bush, which expresses a medium vigor when compared to the bush of the 'EB 8-46' blueberry plant, which expresses a medium to strong vigor. Further, the present, new variety is distinguishable from the 'EB 8-46' blueberry plant in view of its bush growth habit, which expresses a semi-upright growth habit when compared to the bush of the 'EB 8-46' blueberry plant, which has a growth habit which is considered spreading. Still further, the present, new variety is distinguishable from the 'EB 8-46' blueberry plant (a closest known variety) in view of the fruit it produces, which possesses a medium to high fruit sweetness when compared to the fruit produced by the 'EB 8-46' blueberry plant, which produces fruit having a high fruit sweetness. Moreover, the present, new variety is distinguishable from the 'EB 8-46' blueberry plant in view of the fruit it produces, which possess a high fruit firmness when compared to the fruit produced by the 'EB 8-46' blueberry plant, which produces fruit having a high to very high fruit firmness. Yet further, the present, new variety is distinguishable from the 'EB 8-46' blueberry plant in view of its very early bloom time and pick date when compared to the 'EB 8-46' blueberry plant, which has an early bloom time and pick date. Even further, the present, new variety is distinguishable from the 'EB 8-46' blueberry plant (a closest known variety) in view of its bush, which does not produce flowers and fruit on the current year's shoots when compared to the bush of the 'EB 8-46' blueberry plant, which has a bush that does produce flowers and fruit on the current year's shoots.

The present, new variety is distinguishable from the 'SC10' blueberry plant (the seed parent), in view of its bush, which expresses a medium vigor when compared to the bush of the 'SC10' blueberry plant, which expresses a strong vigor. Further, the present, new variety is distinguishable from the 'SC10' blueberry plant in view of the fruit it produces, which possesses a medium to high fruit sweetness when compared to the fruit produced by the 'SC10' blueberry plant, which produces fruit having a high fruit sweetness. Still further, the present, new variety is distinguishable from the 'SC10' blueberry plant (the seed parent) in view of the fruit it produces, which possess a very large fruit size when compared to the fruit produced by the 'SC10' blueberry plant, which produces fruit having a large fruit size. Yet further, the present, new variety is distinguishable from the 'SC10' blueberry plant (the seed parent) in view of its very early bloom time and pick date when compared to the 'SC10' blueberry plant, which has an early bloom time and pick date.

The present, new variety is distinguishable from the 'NS30' blueberry plant (the pollen parent), in view of the fruit it produces, which possesses a medium to high fruit sweetness when compared to the fruit produced by the 'NS30' blueberry plant, which produces a fruit having a high fruit sweetness. Further, the present, new variety is distinguishable from the 'NS30' blueberry plant in view of the fruit it produces, which possesses a medium fruit acidity when compared to the fruit produced by the 'NS30' blueberry plant, which produces fruit having a low fruit acidity. Still further, the present, new variety is distinguishable from the 'NS30' blueberry plant (the pollen parent) in view of the fruit it produces, which possesses a very large fruit size when compared to the fruit produced by the 'NS30' blueberry plant, which produces fruit having a medium fruit size. Yet further, the present, new variety is distinguishable from the 'NS30' blueberry plant (the pollen parent) in view of its very early bloom time when compared to the 'NS30' blueberry plant, which has an early bloom time.

BRIEF DESCRIPTION OF THE DRAWINGS

The accompanying drawings which are provided are color photographs of the new blueberry plant 'NS 14-4' at three year's age.

Figure 1:
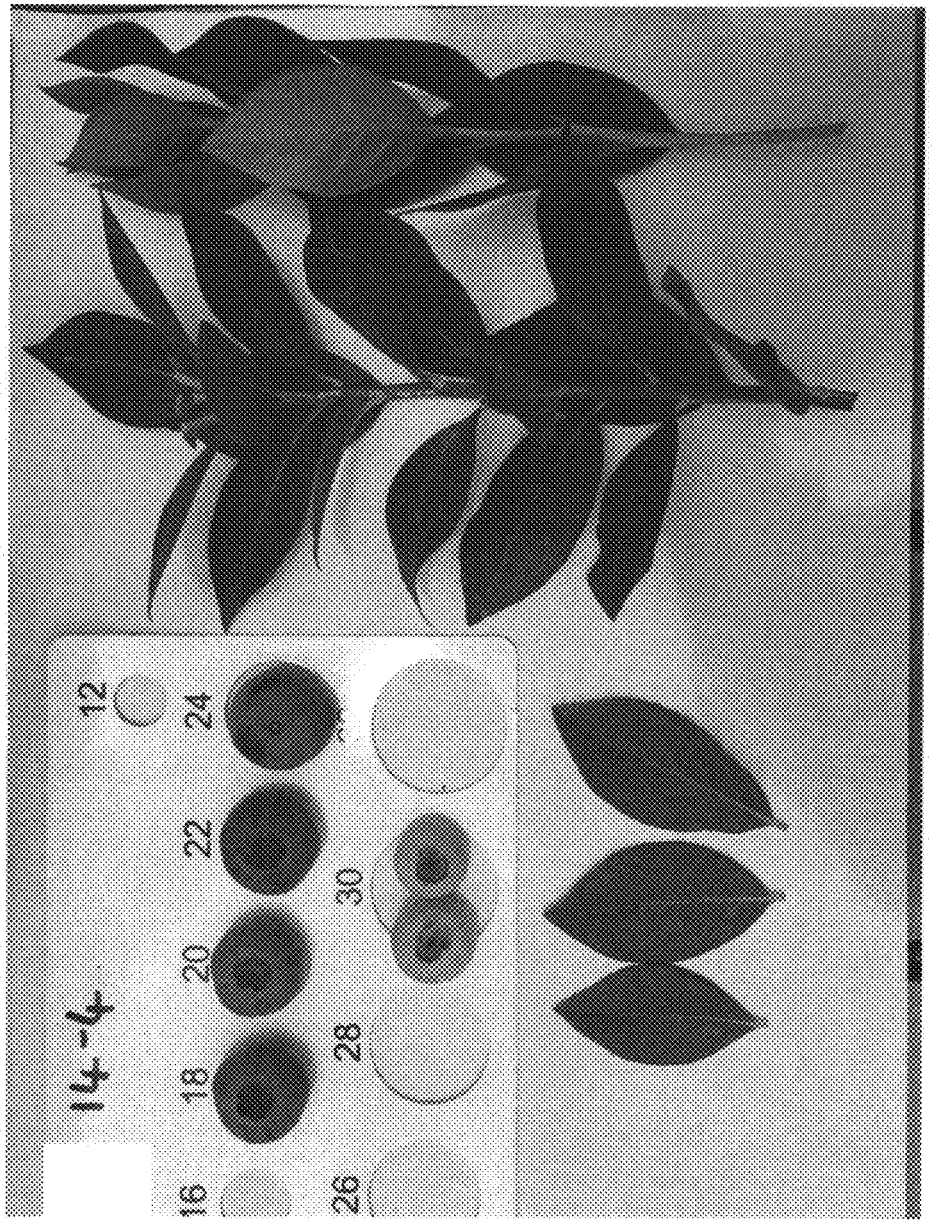
FIG. 1 is a color photograph, which shows the new blueberry plant 'NS 14 4'. This photograph depicts several unripe and ripe fruit, the ripe fruit being sufficiently mature for harvesting and shipment, and further shows typical shoot-bearing leaves, and several leaves showing the dorsal coloration thereof.
Figure 2:
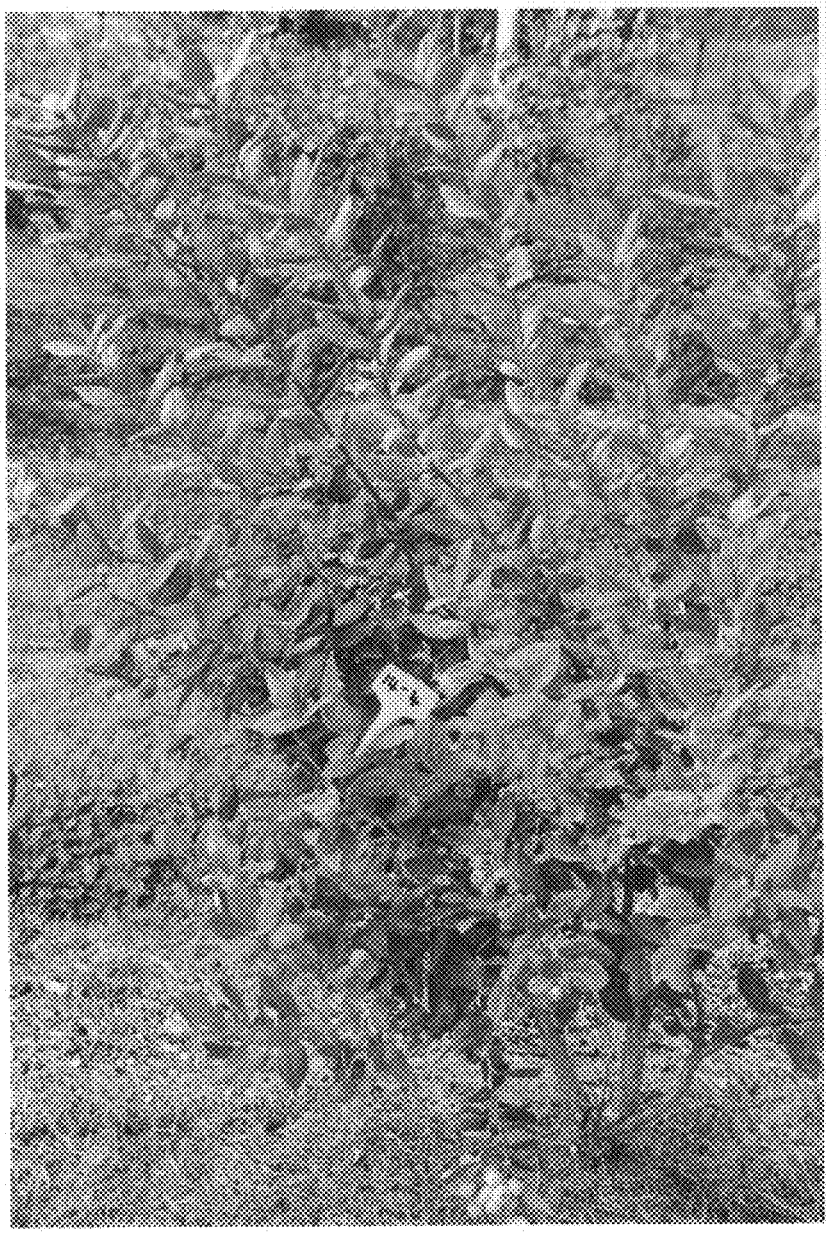
FIG. 2 is a color photograph, which shows the new blueberry plant 'NS 14 4'. This photograph depicts a mature bush with unripe and ripe fruit, the ripe fruit being sufficiently mature for harvesting and shipment, and the semi-upright growth habit of the bush.
Figure 3:
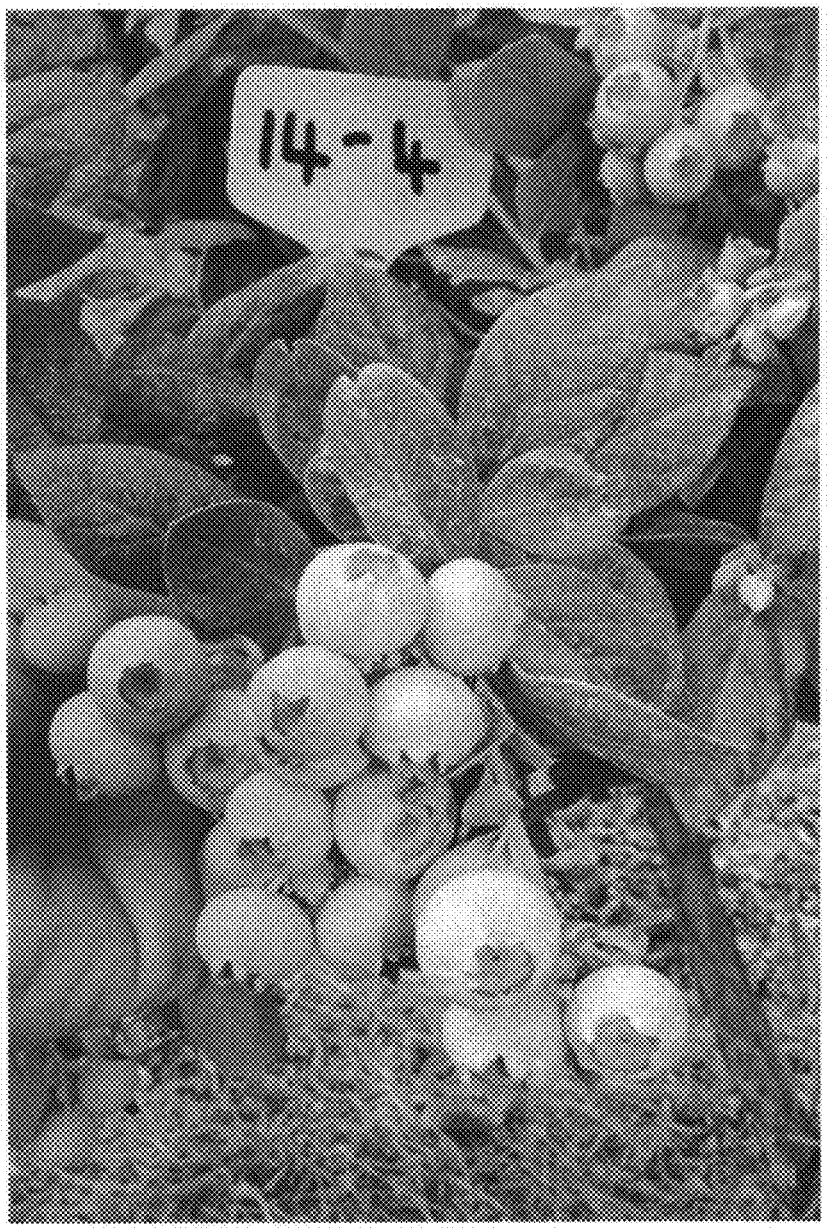
FIG. 3 is a color photograph, which shows the new blueberry plant 'NS 14 4'. This photograph depicts buds and shoots of a mature bush with unripe fruit, and the very large fruit size.

The colors in the attached drawings are as nearly true as reasonably possible in a color representation of this type. Due to chemical development, processing and printing, the leaves and fruit depicted in these photographs may or may not be accurate when compared to the actual specimens. For this reason, future color references should be made to the color plates (Royal Horticultural Society Colour Chart 6th Edition, hereinafter R.H.S.), and the color descriptions as provided, hereinafter.

NOT A COMMERCIAL WARRANTY

The following detailed description has been prepared solely to comply with the provisions of 35 U.S.C. § 112, and does not constitute a commercial warranty (either expressed or implied), that the present, new variety will, in the future, display the botanical horticultural, or other characteristics as set forth, hereinafter. Therefore, this disclosure may not be relied upon to support any future legal claims including, but not limited to, breach of warranty and merchantability, or fitness for any particular purposes, or non-infringement which is directed, in whole, or in part, to the present, new variety.

DETAILED DESCRIPTION

Referring more specifically to the botanical details of this new and distinct variety of blueberry plant, the following has been observed during the fourth growing season under the ecological conditions prevailing at the farm of the inventor, and which is located near Yanchep Springs, Yanchep, Western Australia.

Plant:

*Plant vigor*.—The present, new variety of blueberry plant is considered to display a medium plant vigor.

*Plant growth habit*.—The present, new variety of blueberry plant is considered to display a semi-upright growth habit.

*Size of plant*.—On average, about 1.6 meters by 0.9 meters.

*Internode length—one-year-old shoots*.—About 9.1 mm.

*Bark color*.—Gray Red (RHS 180B).

*Color, one-year-old shoots*.—Yellow Green (RHS 150C).

Leaves:

*Leaf length*.—About 62.0 mm. This is considered an average length.

*Leaf width*.—About 36.0 mm. This is considered an average width.

*Leaf ratio—length/width*.—On average, about 1.72.

*Color of leaf, dorsal surface*.—Yellow Green (RHS 146A).

*Color of leaf, ventral surface*.—Yellow Green (RHS 147C).

*Color of leaf, vein*.—Yellow Green (RHS 149B).

*Venation pattern of leaf*.—Reticulate.

*Leaf apex texture*.—Glabrous.

*Leaf apex shape*.—Acuminate.

*Leaf base shape*.—Cuneate.

*Leaf shape*.—Elliptic.

*Leaf marginal edge*.—Entire.

*Leaf arrangement of plant*.—Alternate.

*Leaf petioles*.—Length — 4.5 mm. Diameter — 2.3 mm. Color — Moderate Yellow Green (RHS 138C).

*Deciduous bud burst, date*.—Not applicable, evergreen.

*Time of vegetative bud burst*.—August-September, under the ecological conditions prevailing near Yanchep Springs, Yanchep, Western Australia.

Flowers:

*Number of flowers*.—About 5 to 7.

*Inflorescence length, excluding peduncle*.—About 18.4 mm.

*Flower bud coloration*.—The presence of anthocyanin is considered very weak in the flower buds.

*Beginning of flowering on one-year-old shoots*.—Considered very early in the growing season.

*Beginning of flowering on current year's shoots*.—Flowering does not occur on the current year's shoots.

*First bloom, date*.—May under the ecological conditions prevailing near Yanchep Springs, Yanchep, Western Australia.

*Bloom time, duration*.—8 weeks under the ecological conditions prevailing near Yanchep Springs, Yanchep, Western Australia.

*Corolla shape*.—Urceolate.

*Corolla ridges*.—Present.

*Corolla tube size*.—Considered medium to large for the variety.

*Corolla length*.—On average, about 9.3 mm.

*Corolla diameter*.—On average, about 9.8 mm.

*Corolla aperture size*.—On average, about 3.8 mm.

*Corolla tube coloration*.—White (RHS 155C).

*Pedicel color*.—Yellow Green (RHS N144D).

*Pedicel length*.—On average, about 13.0 mm.

*Calyx diameter*.—On average, about 6.5 mm.

*Calyx basin depth*.—On average, about 2.5 mm.

*Attitude of sepals*.—Considered to be semi-erect.

*Type of sepals*.—Straight.

Reproductive organs:

*Pollen anthers, size*.—On average, about 4.3 mm.

*Pollen anthers, color*.—Gray Orange (RHS N167B).

*Pistil, length*.—On average, about 9.5 mm.

*Pistil, color*.—Yellow Green (RHS 144C).

*Pollination requirements*.—The variety is self-fertile.

Fruit:

*Unripe fruit, color*.—Yellow Green (RHS N144C).

*Unripe fruit, intensity of green color*.—Considered low to medium for the species.

*Ripe fruit skin, color*.—Bluish Black (RHS 203C).

*Ripe fruit flesh, color*.—Yellow Green (RHS 145C).

*Seeds, color*.—Gray Orange (RHS 167D).

*Fruit size*.—On average, about 20.0 mm in diameter with height 14.5 mm.

*Fruit weight*.—On average, about 4.0 grams.

*Fruit production*.—On two-year-old bush, on average, about 5 kilograms.

*Berry shape*.—Oblate.

*Sweetness, when ripe*.—Considered medium to high.

*Firmness, when ripe*.—Firm.

*Acidity, when ripe*.—Medium for the species.

*Cluster density*.—Medium.

*Storability of the fruit*.—Considered excellent.

*Market use*.—Considered first grade fresh market fruit.

*First pick date*.—August 1, under the ecological conditions prevailing near Yanchep Springs, Yanchep, Western Australia.

*Last pick date*.—October 31, under the ecological conditions prevailing near Yanchep Springs, Yanchep, Western Australia.

*Plant fruiting type*.—Generally speaking, fruiting occurs on one-year-old shoots only.

*Beginning of fruit ripening on one-year-old shoots*.—Considered to be very early in the season.

*Beginning of fruit ripening on current year's shoots*.—Generally, there is no fruit ripening on the current year's shoots.

*Resistance to insects and diseases*.—No particular susceptibilities were noted. The present, new variety has not been tested to expose or detect any susceptibilities resistance to any known plant and/or fruit diseases.

Although the new variety of blueberry plant possesses the described characteristics when grown under the ecological conditions prevailing near Yanchep Springs, Yanchep, Western Australia, it should be understood that the usual variations of the magnitude and characteristics incident to changes in growing conditions, fertilization, pruning, pest control, frost, climactic variables, and horticultural management are to be expected.

Having thus described and illustrated my new variety of blueberry plant, what I claim is new, and desire to secure by plant Letters Patent is:

1. A new and distinct variety of blueberry plant, substantially as illustrated and described, and which is characterized principally as to novelty by producing a fruit having a very large fruit size, high fruit firmness, medium fruit acidity, and a medium to high fruit sweetness, and displaying a small dry picking scar, and a high yield, when grown under the ecological conditions prevailing near Yanchep Springs, Yanchep, Western Australia.

* * * * *